US009382372B2

United States Patent
Matsufuji et al.

(10) Patent No.: US 9,382,372 B2
(45) Date of Patent: Jul. 5, 2016

(54) POLYOL, POLYOL COMPOSITION, AND FLEXIBLE POLYURETHANE FOAM USING THE SAME

(75) Inventors: Mikio Matsufuji, Ichihara (JP); Tamotsu Kunihiro, Kisarazu (JP); Atsushi Miyata, Ichihara (JP); Shinsuke Matsumoto, Ichihara (JP); Koichi Sano, Ichihara (JP); Toru Hiraide, Syunan (JP)

(73) Assignee: MITSUI CHEMICALS & SKC POLYURETHANES INC., Tokyo (JP)

( * ) Notice: Subject to any disclaimer, the term of this patent is extended or adjusted under 35 U.S.C. 154(b) by 235 days.

(21) Appl. No.: 13/814,437

(22) PCT Filed: Aug. 8, 2011

(86) PCT No.: PCT/JP2011/068035
§ 371 (c)(1),
(2), (4) Date: Feb. 5, 2013

(87) PCT Pub. No.: WO2012/018135
PCT Pub. Date: Feb. 9, 2012

(65) Prior Publication Data
US 2013/0131208 A1    May 23, 2013

(30) Foreign Application Priority Data

Aug. 6, 2010  (JP) .................................. 2010-177691

(51) Int. Cl.
| | |
|---|---|
| C08G 18/32 | (2006.01) |
| C08G 18/48 | (2006.01) |
| C08G 18/63 | (2006.01) |
| C08G 18/76 | (2006.01) |
| C07C 31/18 | (2006.01) |
| C08G 18/40 | (2006.01) |
| C07C 41/02 | (2006.01) |
| C07C 41/03 | (2006.01) |
| C07C 43/178 | (2006.01) |
| C08G 101/00 | (2006.01) |

(52) U.S. Cl.
CPC ............ *C08G 18/3212* (2013.01); *C07C 31/18* (2013.01); *C08G 18/3206* (2013.01); *C08G 18/4072* (2013.01); *C08G 18/48* (2013.01); *C08G 18/4841* (2013.01); *C08G 18/632* (2013.01); *C08G 18/7664* (2013.01); *C07C 41/02* (2013.01); *C07C 41/03* (2013.01); *C07C 43/178* (2013.01); *C08G 2101/005* (2013.01); *C08G 2101/0008* (2013.01); *C08G 2101/0083* (2013.01)

(58) Field of Classification Search
CPC ........ C07C 43/178; C07C 41/02; C07C 41/03
See application file for complete search history.

(56) References Cited

U.S. PATENT DOCUMENTS

| | | | |
|---|---|---|---|
| 4,810,535 A | 3/1989 | McCollum et al. | |
| 2001/0031797 A1* | 10/2001 | Kuwamura et al. | ............ 521/155 |
| 2003/0100623 A1 | 5/2003 | Kaku et al. | |
| 2003/0120022 A1* | 6/2003 | Sunder et al. | .................... 528/95 |
| 2008/0085980 A1 | 4/2008 | Sakanishi | |
| 2008/0114088 A1 | 5/2008 | Sasaki et al. | |
| 2009/0239964 A1 | 9/2009 | Sasaki et al. | |

FOREIGN PATENT DOCUMENTS

| | | |
|---|---|---|
| JP | 02-004826 A | 1/1990 |
| JP | 2005-068292 A | 3/2005 |
| JP | 2006-063344 A | 3/2006 |
| JP | 2006-070118 A | 3/2006 |
| JP | 2007-284585 A | 11/2007 |
| JP | 2008-069220 A | 3/2008 |
| JP | 2009-275072 A | 11/2009 |
| WO | WO 2008/038678 A1 | 4/2008 |
| WO | WO 2009/131141 A1 | 10/2009 |

OTHER PUBLICATIONS

International Search Report PCT/JP2011/068035 dated Nov. 1, 2011.
Extended European Search Report received in European Patent Application No. 11814758.6 dated Jul. 21, 2014.

\* cited by examiner

*Primary Examiner* — Melissa Rioja
(74) *Attorney, Agent, or Firm* — Foley & Lardner LLP

(57) ABSTRACT

Disclosed are a polyol with a molecular weight distribution Mw/Mn of 4 or more, obtained by reacting a compound comprising an alkylene oxide compound (II) having a hydroxyl group in a base polyol (I) with a molecular weight of 2000 or more; and a polyol composition for a flexible polyurethane foam, comprising a polyol compound and a crosslinker, wherein the crosslinker comprises a polyol (a) with a hydroxyl value of 50 to 1100 mgKOH/g and with a primary hydroxylate ratio of 25% or more and 60% or less, which is obtained by an addition of a compound comprising alkylene oxide compound (ii) having a hydroxyl group to active hydrogen compound (i).

11 Claims, No Drawings

POLYOL, POLYOL COMPOSITION, AND FLEXIBLE POLYURETHANE FOAM USING THE SAME

TECHNICAL FIELD

The present invention relates to a polyol, a polyol composition, and a flexible polyurethane foam using the same. For more detail, the present invention relates to a polyol which is useful for producing a flexible polyurethane foam having an excellent resilience, a moderate hardness and an excellent durability in a good balance.

BACKGROUND ART

Since flexible polyurethane foams have an excellent cushioning property, they are widely used for the purpose of cushion materials such as seat cushions for vehicles. In particular, since cushion materials having a high resilience can achieve an ideal body pressure dispersion and it is very comfortable, the needs are extremely high. Also, in the seat cushions, there are simultaneously required a moderate hardness that is not too soft and too hard, as well as an excellent durability that there is a little change of the elasticity, the hardness and the thickness even if it is used for a long time.

In late years, in the field of flexible polyurethane foams, in particular of seat cushions for vehicles such as automobiles, a weight saving is required. However, when a weight saving of the flexible polyurethane foam is progressed, the hardness is damaged and the form properties tend to be deteriorated. Thus, various studies regarding maintaining and improving the hardness have been carried out.

As a method for improving the hardness of a flexible polyurethane foam, it is generally known to increase the used amount of a polymer dispersed polyol obtained by dispersing a vinyl polymer in a polyether polyol. However, by this method, another property is deteriorated.

As another method, there is a method using a specified crosslinker. For example, Patent Document 1 discloses a technology in which a polyglycerin is added as a part of a crosslinker to improve a moldability. However, in this method, the sufficient hardness of the flexible polyurethane foam is not developed.

Also, Patent Document 2 discloses a polymerization method of glycidol using an alkali metal halide as a catalyst. However, in this method, a polyol for developing a sufficient property of the flexible polyurethane foam is not obtained.

Also, Patent Document 3 and Patent Document 4 disclose an ester of a fatty acid and a polyglycerin with a primary OH of 50 wt % or more as a composition in a high crystallized material. However, these are not used for a flexible polyurethane foam.

Also, Patent Document 5 discloses a method in which a polyglycerin is used as a crosslinker together with a specified polyol to produce a flexible polyurethane foam. However, in this method, a polyol for developing a sufficient property of the flexible polyurethane foam is not obtained.

Also, Non-Patent Document 1 discloses a cyclic oligoglycidol (C18, 6 glycidol). Also, Non-Patent Document 2 discloses a method for synthesizing a polyglycidol by an addition of glycidol to a monomer having terminal OH. However, these are not used for a flexible polyurethane foam.

PRIOR ART DOCUMENT

Patent Document

Patent Document 1: JP 2003-313267 A
Patent Document 2: JP 2002-30144 A
Patent Document 3: JP 2008-143841 A
Patent Document 4: WO 2006/134886
Patent Document 5: JP 2003-313267 A

Non-Patent Document

Non-Patent Document 1: Reactive & Functional Polymers (2005, 65(3), P 259-)
Non-Patent Document 2: Reviews in Molecular Biotechnology (2002, 90, P 257-)

SUMMARY OF THE INVENTION

Problem to be Solved by the Invention

The present invention was realized in order to solve the above-explained problems. That is, the object of the present invention is to provide a polyol which is useful for producing a flexible polyurethane foam having an excellent resilience, a moderate hardness and an excellent durability in a good balance.

Means of Solving the Problem

The first present invention is a polyol with a molecular weight distribution Mw/Mn of 4 or more, obtained by reacting a compound comprising an alkylene oxide compound (II) having a hydroxyl group in a base polyol (I) with a molecular weight of 2000 or more.

The second present invention is a polyol composition for a flexible polyurethane foam, comprising a polyol compound and a crosslinker, wherein the crosslinker comprises a polyol (a) with a hydroxyl value of 100 to 1100 mgKOH/g and with a primary hydroxylate ratio of 25% or more and 60% or less, which is obtained by an addition of a compound comprising an alkylene oxide compound (ii) having a hydroxyl group to an active hydrogen compound (i).

Effect of the Invention

According to the present invention, even if a weight saving of the flexible polyurethane foam proceeds in response to the weight saving requirements of cushion materials such as car for cushion seats for cars, the properties can be maintained or improved. Specifically, when the polyol or the polyol composition of the present invention is used, a flexible polyurethane foam having an excellent resilience, a moderate hardness and an excellent durability in a good balance can be obtained.

MODE FOR CARRYING OUT THE INVENTION

First, an embodiment of the first present invention is explained.

The polyol of the first present invention is a polyol (hereinafter, referred to as "polyol (A)") with a molecular weight distribution Mw/Mn of 4 or more, which is obtained by reacting a compound containing an alkylene oxide compound (II) having a hydroxyl group in base polyol (I) with a molecular weight of 2000 or more.

The molecular weight distribution curve of the polyol (A) preferably has at least one maximum value in an area of higher molecular weight than that of the base polyol (I). This maximum value is typically caused by a polyol obtained by an addition polymerization of a compound containing the alkylene oxide compound (II) having a hydroxyl group to a hydroxyl group of the base polyol (I).

In the molecular weight distribution curve of the polyol (A), there are typically existed an area S1 of the base polyol (I), an area S2 of higher molecular weight, and an area S3 of lower molecular weight. As mentioned above, the area S2 of higher molecular weight is typically caused by a polyol obtained by an addition polymerization of a compound containing the alkylene oxide compound (II) having a hydroxyl group to a hydroxyl group of the base polyol (I). Also, the area S3 of lower molecular weight is typically caused by a polyol consisting of a polymer of a compound containing the alkylene oxide compound (II) having a hydroxyl group. That is, it can also be said that the polyol (A) is a mixture of these various polyols. In the molecular weight distribution curve, an area ratio (S1/S2) of area S1 and area S2 is preferably 99/1 to 20/80 from the point of the viscosity of the product or the like.

The average functional group number of the polyol (A) is preferably larger than 6. When the average functional group number is larger than 6, the hardness, the resilience and the durability of the flexible polyurethane foam become good. Also, even if this average functional group number is increased to approximately 700, there is an effect for the developing a good balance of the properties. This average functional group number is a value represented by an integer which is calculated by adding, for example, the added mol number of alkylene oxide compound (II) having a hydroxyl group (in the case where the hydroxyl group number of compound (II) is 1) to the functional group number of base polyol (I) and by rounding off it to the nearest integer.

The base polyol (I) is a base polymer to function as an initiator for the addition polymerization reaction of a compound containing the alkylene oxide compound (II). It may be a polymer having a hydroxyl group which functions in that manner, and the kind is not particularly limited. The molecular weight of base polyol (I) is 2000 or more, and is preferably 3000 to 7000.

Examples of the base polyol (I) used for the polyol (A) include, for example, polyether compounds (2) obtained by adding one or more alkylene oxides selected from ethylene oxide, propylene oxide and butylene oxide to an organic compound (1) which has one or more groups selected from hydroxyl group, amino group, thiol group and carboxyl group and which does not have a polyether structure.

Examples of organic compound (1) having a hydroxyl group in a molecule include, for example, alcohols with a carbon number of 1 to 20 having 1 to 8 hydroxyl groups, sugars or derivatives thereof, and aromatic compounds with a carbon number of 6 to 20 having 1 to 3 hydroxyl groups. Among these, alcohols with a carbon number of 1 to 20 having 1 to 8 hydroxyl groups are preferable, and ethyleneglycol, propylene glycol, glycerin, trimethylolpropane, pentaerythritol, sorbitol, sucrose and triethanolamine are more preferable.

Examples of the organic compound (1) having an amino group in a molecule include, for example, aliphatic or aromatic primary amines with a carbon number of 1 to 20, aliphatic or aromatic secondary amines with a carbon number of 2 to 20, polyvalent amines with a carbon number of 2 to 20 having 2 to 3 primary or secondary amino groups in a molecule, saturated cyclic secondary amines with a carbon number of 4 to 20, unsaturated cyclic secondary amines with a carbon number of 4 to 20, and cyclic polyvalent amines with a carbon number of 4 to 20 having 2 to 3 secondary amino groups in a molecule. Among these, aliphatic or aromatic primary amines with a carbon number of 1 to 20 and aliphatic or aromatic secondary amines with a carbon number of 2 to 20 are preferable, and monoethanolamine, diethanolamine, ethylenediamine, piperazines, aniline, toluidine, 2,4-tolylenediamine, 2,6-tolylenediamine, 2,3-tolylenediamine, 4,4'-diaminodiphenylmethane are more preferable.

Compound (II) used for the polyol (A) is an alkylene oxide compound having a hydroxyl group. The carbon number of the alkylene oxide is preferably 2 to 12. Specific examples thereof include 2-hydroxytetrahydrofuran, 3-hydroxyoxetane, glycidol, 1,2-epoxy-3-butanol, 3-hydroxycyclopentene oxide, 2,3-epoxy-2-methyl-1-propanol, 2,3-epoxybutanol, 3,4-epoxy-3-methyl-2-pentanol, 3,4-epoxy-4-methyl-2-pentanol, 2,3-epoxycyclohexanol, 2,3-epoxy-4-hydroxyhexane, 6-oxabicyclo[3.1.0]hexane-2,4-diol, 6-oxabicyclo[3.1.0]hexane-2,3-diol, 2,3-epoxy-1,4-butanediol, 1,2-epoxy-3-pentanol, and 2,3-epoxy-4-heptanol. Among these, epoxides having a hydroxyl group are preferable, and glycidol is particularly preferable. Also, glycidol and an alkylene oxide other than it may be used together, Further, the alkylene oxide compound (II) which has a hydroxyl group and an alkylene oxide which does not have a hydroxyl group may be used together. That is, an alkylene oxide compound containing the alkylene oxide compound (II) having a hydroxyl group may be reacted in the base polyol (I). Specific examples of the alkylene oxide which does not have a hydroxyl group include ethylene oxide, propylene oxide, 1,2-butylene oxide, 2,3-butylene oxide, styrene oxide, cyclohexane oxide, epichlorohydrin, epibromohydrin, methyl glycidyl ether, allyl glycidyl ether, and phenyl glycidyl ether. Among these, ethylene oxide, propylene oxide, 1,2-butylene oxide, 2,3-butylene oxide and styrene oxide are preferable. In particular, ethylene oxide, propylene oxide, 1,2-butylene oxide and 2,3-butylene oxide are more preferable.

Some alkylene oxides having a hydroxyl group such as glycidol contain an anion-containing impurity such as chlorine ($\alpha$-chlorohydrin in the case of glycidol) depending on the production method. The alkylene oxides containing such an impurity can be used in the present invention. In this case, the polymerization is carried out with keeping the reaction system basic that the mol number of the anion such as chlorine does not become larger than the mal number of the cation of the polymerization catalyst described below.

The amount of glycidol is preferably 50 to 100 mol % in 100 mol % of the compound containing the alkylene oxide compound (II) having a hydroxyl group. When the amount is 50 mol % or more, the effect regarding the hardness of the flexible polyurethane foam is sufficiently developed and the balance of the properties becomes good.

Specific examples of the reaction for addition polymerization of the compound containing the alkylene oxide compound (II) having a hydroxyl group to the base polyol (I) include, for example, a method by a simultaneous addition polymerization of a mixture consisting of glycidol and an alkylene oxide other than glycidol in a random form, a method by an addition polymerization of only glycidol, a method by an addition polymerization of glycidol in a block form and thereafter by an addition polymerization of an alkylene oxide other than glycidol in a block form, and a method by addition polymerizations of glycidol and of an alkylene oxide other than glycidol in a sequential block form.

In the alkylene oxide contained in the whole of the polyol (A), the mol ratio of the alkylene oxide other than glycidol and glycidol is preferably 99/1 to 20/80.

When the compound containing the alkylene oxide compound (II) having a hydroxyl group is reacted in the base polyol (I) to obtain the polyol (A), it is preferable to use a basic compound as a catalyst. By a reaction in the presence of a basic compound, above-explained suitable polyol (A) can be obtained well.

Specific examples of the basic compound include alkali metal compounds and alkaline-earth metal compounds such as hydroxides and carbonates, and tertiary amine compounds such as triethylamine, dimethyloctylamine, dimethylpalmitylamine, phosphazene compounds and phosphazenium compounds.

As a phosphazene compound, it is possible to use, for example, a compound represented by following formula (2) described in JP 2001-106780 A.

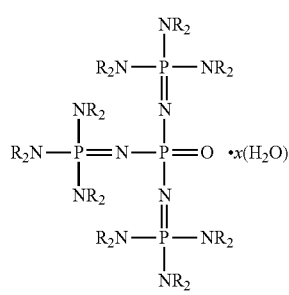

[In formula (2), R each independently represent a hydrocarbon group with a carbon number of 1 to 10, and x is a content (mol ratio) of water contained and represents 0 to 5.]

Compound represented by above-mentioned formula (2) is typically tris[tris(dimethylamino)phosphoranylideneamino] phosphine oxide or tris[tris(diethylamino)phosphoranylideneamino]phosphine oxide.

As a phosphazenium compound, it is possible to use, for example, a compound represented by following formula (1) described in JP 2001-106780 A.

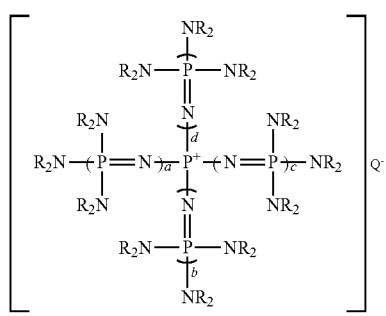

[In formula (1), a, b, c and d each are an integer of 0 to 3. However, it is excluded that all of a, b, c and d are 0. R each independently represent a hydrocarbon group with a carbon number of 1 to 10, and it is included that two R on the same nitrogen atom are connected each other to form a ring structure. Q⁻ represents hydroxy anion, an alkoxy anion, an aryloxy anion or an carboxy anion.]

Compound represented by above-mentioned formula (1) is typically tetrakis[tris(dimethylamino)phosphoranylideneamino]phosphonium hydroxide, tetrakis[tris(dimethylamino)phosphoranylideneamino]phosphonium methoxide, tetrakis[tris(dimethylamino)phosphoranylideneamino]phosphonium ethoxide, or tetrakis[tri(pyrrolidine-1-yl)phosphoranylideneamino]phosphonium tert-butoxide.

The lower limit of the used amount of the basic compound for the reaction is 0.0001 mol % with respect to 1 mol of the active hydrogen in the polyol (A), is preferably 0.0005 mol %, and is more preferably 0.001 mol % white the upper limit is 10 mol %, is preferably 1 mol %, and is more preferably 0.5 mol %. If the amount of the basic compound is less than the above-mentioned range, the reaction time becomes longer. Also, if it is more than the above-mentioned range, the production is not economically preferable. And, in the case where the post processing is carried out, the neutralization salt is hardly removed, and a polyether polyol, by which a good balance of the properties of the flexible polyurethane foam physical property is developed, cannot be obtained.

Also, when an alkylene oxide containing an anion-containing impurity is used as described above, it is preferable to carry out the polymerization with keeping a reaction system basic. if the reaction system is not basic, the molecular weight distribution becomes narrow and the high molecular weight body is tend not to be formed.

It is desirable to sequentially charge an alkylene oxide having a hydroxyl group to a reaction system. in the case where an alkylene oxide having a hydroxyl group stays in a reaction system in a large amount, a self-polymerization preferentially occurs and a high molecular weight body is hardly formed, and the molecular weight distribution tends to become narrow. Thus, it desirably takes a certain time to charge it. Further, the initial concentration a of the catalyst cation to OH of a base polyol that is an initiator is preferably higher, depending on catalytic activity, because the reaction of the base polyol and alkylene oxide (II) having a hydroxyl group is promoted. Also, when the OH concentration (mol/kg) in the initiator is higher, the reaction with alkylene oxide (II) having a hydroxyl group is promoted, and it is preferable.

In view of these, when the initial concentration of the catalyst cation to OH of the initiator is a (mol/initiator OH mol), the concentration of the initiator OH is β (mol/kg), and the charging speed of the alkylene oxide having a hydroxyl group is γ (mol/Hr·kg), γ/(α×β) is preferably 20000 or less and is more preferably 10000 or less because a high molecular weight body can definitely be formed.

The reaction conditions are not particularly limited, but the temperature is preferably 80 to 160° C. and is more preferably 90 to 140° C. Also, the pressure is preferably 0.5 MPaG or less.

In the case where the above-mentioned basic compound is used as a catalyst, a step for removing a catalyst from the polyol (A) obtained may be carried out, or may not be carried out. In both cases, the polyol (A) can be used for producing a flexible polyurethane foam.

The polyol (A) can be mixed with another polyol to be used. In particular, a polyol composition containing 1 to 200 parts by mass of the polyol (A) and 100 parts by mass of polyol (B) with a hydroxyl value of 10 to 80 mgKOH/g is preferable, and a polyol composition containing 1 to 100 parts by mass of the polyol (A) and 100 parts by mass of polyol (B) with a hydroxyl value of 10 to 80 mgKOH/g is more preferable. This polyol (B) is particularly preferably at least one polyol selected from polyether polyols and polymer dispersed polyols.

Next, the second present invention is explained.

The second present invention is a polyol composition for a flexible polyurethane foam, which contains a polyol compound and a crosslinker, in which the crosslinker contains the polyol (a) with a hydroxyl value of 50 to 1100 mgKOH/g and with a primary hydroxylate ratio of 25% or more and 60% or less, which is obtained by an addition of a compound containing the alkylene oxide compound (ii) having a hydroxyl group to active hydrogen compound (i).

Active hydrogen compound (i) used for the polyol (a) is a compound having an active hydrogen showing reactivity. Examples of active hydrogen compound (i) include, for example, the organic compounds (1) which have one or more groups selected from hydroxyl group, amino group, thiol group and carboxyl group and which do not have a polyether structure. Also, examples include the polyether compounds (2) which are obtained by adding one or more alkylene oxides selected from ethylene oxide, propylene oxide and butylene oxide to this organic compound (1). In particular, an organic compound having a hydroxyl group or an amino group, or having a hydroxyl group and an amino group is preferable, and an organic compound having 1 to 8 hydroxyl groups or amino groups, or having 1 to 8 hydroxyl groups and amino groups is more preferable. Specific examples of this organic compound (1) include the same compounds as those described in the explanation of the first invention. And, active hydrogen compound (i) can be used alone, or in a mixture with two or more kinds, which is selected from the group consisting of the organic compounds (1), water, ammonia, and the polyether compounds (2). Also, active hydrogen compound (i) preferably contains glycerin or glycidol. In the case where active hydrogen compound (i) is glycidol, glycidol functions as both of compound (i) and compound (ii).

The kind, the reaction conditions and the catalyst of compound (ii) used for the polyol (a) are the same as the kind, the reaction conditions and the catalyst of compound (II) in the first invention.

The lower limit of the hydroxyl value of the polyol (a) is 50 mgKOH/g, and is preferably 100 mgKOH/g from the point of the hardness of the flexible polyurethane foam. Also, the upper limit 1100 mgKOH/g, is preferably 1050 mgKOH/g, and is more preferably 1000 mgKOH/g from the points that the hardness of the flexible polyurethane foam is moderately suppressed and that the balance of resilience and durability is made good.

The lower limit of the primary hydroxylate ratio of the polyol (a) is 25%, is preferably 40%, and is more preferably 45% from the point that the balance of the foam properties is made good. Also, the upper limit is 60%, is preferably 58%, and is more preferably 57% from the point that the balance of the foam properties is made good.

The polyol (A) of the first invention and the polyol (a) used in the second invention explained above are purified as necessary. After a basic compound in the crude polyol is neutralized with an acid such as an inorganic acid, a purification step, in which a salt precipitated by dehydration and drying is filtered, can be carried out to produce the polyol.

The catalyst can be adsorbed by an inorganic adsorbent, and the basic compound can be filtered. Also, after it is neutralized with an acid such as an inorganic acid, the surplus acidic component and basic component are adsorbed by an inorganic adsorbent, and it can be filtered. Examples of the inorganic adsorbent include, for example, synthetic silicates (such as magnesium silicate and aluminum silicate), ion exchange resins, and activated white earths.

Also, a well-known stabilizer may be added as necessary before or after the purification of the polyols (A) and (a). In the case where the polyols (A) and (a) are stored for a long time, an antioxidant or an anticorrosive can be added to prevent the deterioration of polyols (A) and (a). In particular, an antioxidant is preferably added to prevent the deterioration of polyols (A) and (a). The antioxidant may be used alone, or in combination with two or more kinds. Examples of the antioxidant include, for example, tert-butyl hydroxy toluene (BHT), pentaerythrityl-tetrakis-3-(3,5-di-tert-butyl-4-hydroxyphenyl)propionate, octadecyl-3-(3,5-di-tert-butyl-4-hydroxyphenyl)propionate, ethylhexylphosphite, tri(nonylphenyl)phosphite, 4,4'-bis-$\alpha,\alpha'$-dimethylbenzyldiphenylamine, 2-tert-butyl-4-ethylphenol, and 2,6-di-tert-butyl-4-ethylphenol.

The added amount of the antioxidant is not particularly limited as long as the effect can be obtained in the concentration, but is usually approximately 100 to 5000 ppm to the polyols (A) and (a). For example, as a stabilizer, at least one selected from the group consisting of hindered phenol compounds and nitrogen-containing compounds can be used. in the case where a stabilizer is used, the added amount is not particularly limited as long as the effect can be obtained in the concentration, but is usually approximately 100 to 5000 ppm to the polyols (A) and (a).

<Polyol Composition>

The polyol (A) of the first invention and the polyol (a) used in the second invention explained above are preferably used as a polyol composition mixed with another polyol.

As another polyol, all polyol compounds commonly used for a polyurethane foam purpose can be used. Specific examples thereof include polyether polyols, polyester polyols, polyester ether polyols, polycarbonate polyols, polybutadiene polyols, bio polyols derived from a nature fat described in WO 2007/020904, WO 2010/013710 and the like, and polymer dispersed polyols. in particular, in order to produce a flexible polyurethane foam used for the purpose of seat pads for vehicles such as automobiles, one or more polyols selected from polyether polyols and polymer dispersed polyols are preferably used as another polyol.

Examples of the polyether polyols and polymer dispersed polyols also include polyols described in JP 2001-107680 A. For example, as a polyether polyol, the polyether compound (2) explained in the second invention can also be used.

The polymer dispersed polyol is a polyol in which a vinyl polymer particle obtained by a radical polymerization of a compound having an unsaturated bond in a polyol is dispersed in this polyol. In particular, a polymer dispersed polyol is preferable. Polymer dispersed polyol provided from polyether polyol obtained from a polyether polyol is preferable. Examples of the radical polymerization initiator used for the polymerization include, for example, azo compounds such as azobisisobutyronitrile and peroxide compounds such as benzoyl peroxide, dialkyl peroxides and peroxy ketals. Also, in the polymerization, a dispersion stabilizer and a chain transfer agent may be added. The vinyl polymer particle dispersed in this polyol is a particle consisting of a polymer of a compound having an unsaturated bond. However, at least a part of this compound is preferably polymerized with a polyether polyol at the time of the polymerization. Specific examples of the compound having an unsaturated bond include (meth)acrylonitrile, styrene, vinyl pyridine, (meth)acrylamide, and (meth)acrylates such as methyl(meth)acrylate and 2-hydroxyethyl(meth)acrylate. This may be used alone, or in a mixture with two or more kinds In the present invention, the preferred polyol compositions include a polyol composition containing the polyol (A) and the polyol (B) with a hydroxyl value of 10 to 80 mgKOH/g and a polyol composition containing the polyol (a) and the polyol (b) with a hydroxyl value of 10 to 80 mgKOH/g. As mentioned above, the polyols (B) and (b) are preferably one or more polyol selected from polyether polyols and polymer dispersed polyols. Also, when the amount of polyols (B) and (b) is assumed to be 100 parts by mass, the amount of polyols (A) and (a) is preferably 1 to 200 parts by mass and is more preferably 1 to 100 parts by mass. Further, in 100 mass % of polyol composition, 0.5 to 20 mass % of a constitutional unit consisting of an alkylene oxide having a hydroxyl group is preferably contained.

The lower limit of the hydroxyl value of polyols (B) and (b) is 10 mgKOH/g, is preferably 15 mgKOH/g, and is more preferably 20 mgKOH/g. Also, the upper limit is 80 mgKOH/g, is preferably 70 mgKOH/g, and is more preferably 60 mgKOH/g. Each lower limit is valid at the point that the flexible polyurethane foam is made not too soft, and each upper limit is valid at the point that the flexible polyurethane foam is made not too hard, i.e. the hardness is not too high. The moderate hardness is important for the purpose of seats for vehicles.

The polyols (B) and (b) may be a mixture of two or more polyols. In that case, the average hydroxyl value of the mixture should be within the above-mentioned range. Also, a polyol other than the polyols (A) and (a) and the polyols (B) and (b) may be used as long as it does not affect the foam property.

<Flexible Polyurethane Foam>

A flexible polyurethane foam is obtained by reacting a polyol composition containing the polyol (A) and/or the polyol (a) explained above with an isocyanate compound. The reaction is carried out in the presence of for example, an arbitrary component such as a catalyst, a foaming agent, a surfactant, or another auxiliary agent <Isocyanate Compound>

The isocyanate compound is not particularly limited. For example, a well-known isocyanate compound, which is described in Keiji Iwata, "Polyurethane Resin Handbook", first edition, Nikkan Kogyo Shimbun Ltd., (1987) pp. 71-98, can be used.

The isocyanate compound for obtaining a foam is preferably toluoylene diisocyanate (the isomer ratio such as 2,4-body and 2,6-body is not particularly limited but 2,4-body/2,6-body is preferably a ratio of 80/20), a polymethylene polyphenyl polyisocyanate (for example, produced by Mitsui Chemicals, Inc., trade name: COSMONATE M-200) or a urethane modified body thereof, or a mixture thereof.

Also, diphenylmethane diisocyanate (for example, produced by Mitsui Chemicals, Inc., trade name: COSMONATE PH), xylylene diisocyanate, norbornene diisocyanate, naphthalene diisocyanate, bis(isocyanatomethyl)cyclohexane or hexamethylene diisocyanate can be used.

In the case where a mixture of toluoylene diisocyanate and another isocyanate compound is used, from a point of the balance of the durability and the mechanical strength of the flexible polyurethane foam, the content of toluoylene diisocyanate in 100 mass % of the total amount of the isocyanate compounds is preferably 50 to 99 mass %, is more preferably 70 to 90 mass %, and is particularly preferably 75 to 85 mass %.

<Catalyst for Producing Flexible Polyurethane Foam>

When a flexible polyurethane foam is produced, a well-known catalyst can be used without a particular limitation. For example, aliphatic amines such as triethylenediamine, bis(2-dimethylaminoethyl)ether, 1-isobutyl-2-methyl imidazole, and morpholine; and organic tin compounds such as tin octanoate and dibutyl tin ditaurate are preferable. This may be used alone, or in combination with two or more kinds. The used amount of the catalyst for producing a flexible polyurethane foam is preferably 0.1 to 10 parts by mass with respect to 100 parts by mass of the polyol composition.

<Foaming Agent>

When a flexible polyurethane foam is produced, a physical foaming agent such as liquefied carbon dioxide can be used as a foaming agent, but water is most preferably used. In the case where water is used as a foaming agent, from a point of the foaming stability and the validity, the used amount of water is preferably 1.3 to 6.0 parts by mass with respect to 100 parts by mass of the polyol composition, is more preferably 1.8 to 5.0 parts by mass, and is particularly preferably 2.0 to 4.5 parts by mass. Also, a physical foaming agent such as a hydroxy fluorocarbon (HFC-245fa or the like) which is developed for the purpose of global environment protection, a hydrocarbon (cyclopentane or the like), carbon dioxide, or liquefied carbon dioxide can also be used together with water. In particular, from a point of reducing the environmental load, it is preferable to use carbon dioxide or liquefied carbon dioxide with water.

<Surfactant>

When a flexible polyurethane foam is produced, a well-known surfactant can be used without a particular limitation. Usually, it is preferable to use an organic silicon surfactant. Examples of the preferred commercial surfactant include, for example, SZ-1966, SZ-1919, SZ-1959, SZ-1142 and SRX-274DL produced by Dow Corning Toray Co., Ltd., L-5309, Y-10366, L-3622, L-598 and L-3150 produced by Momentive Performance Materials Japan limited liability company. The used amount of the surfactant is preferably 0.1 to 10 parts by mass with respect to 100 parts by mass of the polyol composition, and is more preferably 0.5 to 5 parts by mass.

<Auxiliary Agent>

When a flexible polyurethane foam is produced, a general auxiliary agent or an additive for producing a flexible polyurethane foam can be used with each above mentioned component as long as the object of the present invention is not damaged. Examples of the auxiliary agent and the additive include, for example, chain extenders, crosslinkers, cell openers, flame retardants, pigments, UV absorbers, and antioxidants. Specifically, various auxiliary agents and additives, which are described in Nobutaka Matsudaira and Tetsuro Maeda, "Polyurethane", eighth edition, Maki Shoten, (1964) pp. 134-137 and in Hitoshi Matsuo, Nobuaki Kunli, and Kiyoshi Tanabe, "Functional Polyurethane", first edition, CMC Publishing CO., LTD (1989) pp. 54-68, can be used.

<Method for Producing Flexible Polyurethane Foam>

The method for producing flexible polyurethane foam is not particularly limited and a well-known method can be adopted. Specifically, any of a slab foam method, a hot cure mold foam method, and a cold cure mold foam method can be adopted. In the case of producing a seat pad for vehicles such as automobiles, a cold cure mold foam method is preferable.

As the cold cure mold foam method, a well-known method can be adopted. For example, there is a method in which each component such as a polyol, a foaming agent, a catalyst, a surfactant, another auxiliary agent, and a crosslinker is previously mixed to prepare a resin premix, and this resin premix is mixed with an isocyanate compound using a high pressure foaming machine or a low pressure foaming machine so that it comes to have a predetermined NCO index, and the mixture is injected into a mold and is reacted and cured to obtain a flexible polyurethane foam in a certain shape. Here, the NCO index is the value obtained by dividing the mol number of the isocyanate group contained in the isocyanate compound by the active hydrogen group contained in the resin premix. The value of the NCO index is not limited as long as a foam is formed, but it is preferably 0.70 to 1.50 and is more preferably 0.80 to 1.25.

The reaction curing time is usually 30 seconds to 30 minutes, the mold temperature is usually room temperature to approximately 80° C., and the curing temperature is preferably approximately 150° C. Further, after the curing, the cured material may be heated at 80 to 180° C. as long as the object of the present invention is not damaged.

The resin premix is usually mixed with the isocyanate compound by a high pressure foaming machine or a low pressure foaming machine. However, in the case where a hydrolyzable compound such as an organic tin catalyst is used as a catalyst and the foaming agent contains water, in order to prevent a contact with the water, the water component and the organic tin component are injected to a foaming machine in a different path and they are mixed at a mixing head of the foaming machine.

According to the present invention, a flexible polyurethane foam having a high resilience, a moderate hardness and an excellent durability in a good balance can be obtained. In general, the resilience, the hardness and the durability required to the flexible polyurethane foam are different by the purpose. However, the flexible polyurethane foam of the present invention is preferably used for the purpose of cushion materials requiring a high resilience, in particular for the purpose of seat cushions, seat backs, instrument panels, headrests and armrests for vehicles such as automobiles, for the purpose of bedding or furniture, and for the purpose of clothes.

For example, in general, for the purpose of seat cushions for vehicles such as automobiles whose core density is 30 to 75 kg/m$^3$, the hardness (25% ILD) required to the flexible polyurethane foam is preferably 140 to 350 N/314 cm$^2$, and is more preferably 175 to 330 N 1314 cm$^2$. Also, the resilience is preferably 50 to 80%, is more preferably 55 to 77%, and is particularly preferably 60 to 75%. Also, the durability (humid aged compression set) is preferably 25% or less and is more preferably 19% or less.

EXAMPLE

As follows, the present invention is explained in detail by the Examples, but the present invention is not limited to these Examples. "Part(s)" and "%" in the Examples respectively represent "part(s) by mass" and "mass %". The analyses and the measurements in the Examples and the Comparative Examples were carried out according to the following methods.

[Analyses and Measurements Regarding Polyol]
(1) Hydroxyl Value (OHV):
The hydroxyl value (mgKOH/g) was measured according to the method described in JIS K 1557-1.
(2) Total Unsaturation Degree:
The total unsaturation degree was measured according to the method described in JIS K 1557-3.
(3) Viscosity:
The viscosity (mPa·s/25° C.) was measured using a cone-plane rotational viscometer (E-type viscometer),
(4) Molecular Weight (Mp, Mw and Mn):
The molecular weight of the polyol in TABLE 1 to TABLE 3 was measured under the following conditions using a GPC system produced by TOSOH CORPORATION, and the standard polystyrene converted molecular weight was obtained.
Equipment: HLC-8320 GPC,
Column: two TSK-GEL α-M (7.8 mm×300 mm),
Eluent: 0.01 mol-LiBr/1000 ml-DMAc,
Flow rate: 0.6 ml/min,
Detector: RI detector, and
Column temperature: 40° C.
The molecular weight of the polyol in TABLE 11 was measured under the following conditions using a GPC system produced by TOSOH CORPORATION, and the standard polystyrene converted molecular weight was obtained.

Equipment: HLC-8320 GPC,
Column: two TSK-GEL α-M (7.8 mm×300 mm),
Eluent: 0.01 mol-LiBr/1000 ml-DMF,
Flow rate: 0.6 ml/min,
Detector: RI detector, and
Column temperature: 40° C.
(5) Molecular Weight Distribution (Mw/Mn):
This was obtained by calculation from the molecular weights Mw and Mn measured by the above-mentioned method.
(6) Area Ratio (S1) of Base Polyol, Area Ratio (S2) of High Molecular Weight Side, and Area Ratio (S3) of Lower Molecular Weight Side:
As for the polyol in TABLE 1 to TABLE 3, the peaks in the higher molecular weight side and the lower molecular weight side than the peak of the base polyol were identified from the measurement result by GPC. The boundary between the peak of the base polyol and the peak of the higher molecular weight side was assumed to be a minimum point in the higher molecular weight side than the peak of the base polyol which was nearest to the peak of the base polyol, and the boundary between the peak of the base polyol and the peak of the lower molecular weight side was assumed to be a minimum point in the lower molecular weight side than the peak of the base polyol which was nearest to the peak of the base polyol. When the total area of the peaks of the base polyol, the higher molecular weight side and the lower molecular weight side were 100, the area ratios of the peaks were respectively S1, S2 and S3.
(7) Appearance:
The appearance of the polyether polyol was observed by visual inspection at normal temperature, and the condition and color were observed.
(8) Concentration of Residual Catalyst (mol %/Active Hydrogen):
The concentration of the residual catalyst is a concentration of the residual cation in the polyol such as tetrakis[tris(dimethylamino)phosphoranylideneamino]phosphonium (hereinafter, referred to as PZN) or potassium to the active hydrogen. If necessary, it was obtained as follow. In the case of PZN, it was obtained by conducting a $^1$H-NMR measurement using a nuclear magnetic resonance apparatus AL-400 produced by JEOL data Ltd. The chemical shift of the proton of the methyl group in PZN is around 2.7 ppm, and the concentration can be calculated by a comparison with a known concentration PZN and by a comparison with the active hydrogen concentration of polyether polyol (A) and polyol B-1. Also, in the case of a cation except PZN, the concentration was obtained by conducting an analysis by a known suitable method such as an ion chromatography, an ICP emission analysis, or an elemental analysis.
(9) Primary Hydroxylate Ratio (Primary OH-Ate Ratio):
The primary hydroxylate ratio (%) was measured according to the method described in JP 2000-344881 A.
(10) Moisture:
This was measured according to the method described in JIS K 1557-2.
(11) Charging Speed:
The charging speed of the alkylene oxide having a hydroxyl group to the system was obtained as follows.

Charging speed=γ/(α×β)

γ: the charging speed of the alkylene oxide having a hydroxyl group to the system (mol/Hr·kg)=the mol number of the alkylene oxide having a hydroxyl group which is charged in an hour in 1 kg of the initiator which exists in the system α: the concentration of the catalyst cation (mol/initiator OH)=the mol number of the cation in 1 mol of OH contained in the polyol with a molecular weight of 2000 or more that is an initiator β: the concentration of the initiator OH (mol/kg)=the mol number of OH contained in 1 kg of the initiator

[Analyses and Measurements Regarding Polyurethane Foam]

(12) Core Density (Density Core):

The surface skin was removed from the flexible polyurethane foam sample to prepare a cuboid foam sample, and the core density (kg/m$^3$) was measured according to the method for measuring an apparent density described in JIS K 7222.

(13) Hardness (25% ILD):

The hardness (N/314 cm$^2$) of the flexible polyurethane foam with a thickness of 100 mm was measured according to the D method described in JIS K 6400-2.

(14) Tensile Strength:

The tensile strength [stress at the maximum point (kPa)] was measured according to the method described in JIS K 6400-5.

(15) Elongation:

The elongation (%) was measured according to the method described in JIS K 6400-5.

(16) Tear Strength:

The tear strength (N/cm) was measured according to the method described in JIS K 6400-5.

(17) Humid Aged Compression Set (50% Wet Set):

The humid aged compression set (%) was measured according to the method described in JIS K 6400-4. Specifically, a core part of the flexible polyurethane foam molded was cut out to 50 mm×50 mm×25 mm to produce a specimen. This specimen was compressed to the 50% thickness and was sandwiched between parallel plane plates, and it was left as it was at 50° C. under the condition of the relative humidity of 95% for 22 hours. The specimen was taken out and, 30 minutes later, the thickness was measured and the distortion rate (%) was measured by comparing it with the thickness before the test.

(18) Ball Rebound (Core):

The repulsion elastic modulus (%) was measured according to the method described in JIS K 6400-3.

As follows, Example A of the first invention is described.
<Production of Polyol A>

Examples A1 to A5

The base polyol (I) used for the present Example was produced as follows. First, to an alcoholate obtained by adding 0.10 mol of KOH with respect to 1 mol of hydroxyl group in propylene glycol (functional group number f=2), glycerin (functional group number f=3) or pentaerythritol (functional group number f=4) and by dehydrating it under a reduced pressure at 100° C. for 6 hours, an addition polymerization of propylene oxide (PO) was carried out in an autoclave at a reaction temperature of 110° C. under a maximum reaction pressure of 0.4 MPaG. Then, an addition polymerization of ethylene oxide (EO) was carried out at a reaction temperature of 100° C. under a maximum reaction pressure of 0.4 MPaG so that the content of EO in the whole came to be the value shown in TABLE 1, to obtain a crude base polyol. 1.02 equivalents of phosphoric acid with respect to potassium in this crude base polyol and 5 parts of water with respect to 100 parts of the crude base polyol were added, and it was neutralized at 90° C. for 1 hour. Then, it was dehydrated at 110° C. under a reduced pressure so that the water content came to be 500 ppm and the precipitated neutralized salt was filtered to obtain the base polyol (I).

To an alcoholate which was obtained by supplying PZN so that the catalyst cation concentration came to be a (mol/OH) with respect to OH of this base polyol (I) and by dehydrating it under a reduced pressure at 100° C. for 6 hours, glycidol was supplied under the conditions shown in TABLE 1 and an aging was carried out to obtain polyols A1 to A5.

Examples A6 to A8

To an alcoholate which was obtained by adding 0.005 mol of PZN with respect to 1 mol of glycerin and by dehydrating it under a reduced pressure at 100° C. for 6 hours, an addition polymerization of PO was carried out in an autoclave at a reaction temperature of 90° C. under a maximum reaction pressure of OA MPaG. Then, an addition polymerization of EO was carried out at a reaction temperature of 100° C. under a maximum reaction pressure of 0.4 MPaG so that the content of EO in the whole came to be the EO content in TABLE 1, to obtain polyol I-1 that was the base polyol (I). The total unsaturation degree of this polyol I-1 was 0.020 meq/g, the hydroxyl value was 34 mgKOH/g, the residual catalyst concentration was 0.18 mol %/active hydrogen. To this, glycidol was supplied under the conditions shown in TABLE 1 and an aging was carried out to obtain polyols A6 to A8.

Example A9

To an alcoholate which was obtained by supplying KOH so that the catalyst cation concentration came to be a (mol/OH) with respect to OH of the base polyol (I) shown in TABLE 2 and by dehydrating it under a reduced pressure at 100° C. for 6 hours, glycidol containing 1.68% of chlorohydrin as an impurity was supplied and an aging was carried out to obtain polyol A9.

Example A10

To an alcoholate which was obtained by supplying KOH so that the catalyst cation concentration came to be a (mol/OH) with respect to OH of the base polyol (I) shown in TABLE 2 and by dehydrating it under a reduced pressure at 100° C. for 6 hours, glycidol containing 0.5% of chlorohydrin as an impurity was supplied and an aging was carried out to obtain polyol A10.

Example A11

An alcoholate which was obtained by supplying KOH so that the catalyst cation concentration came to be a (mol/OH) with respect to OH of the base polyol (I) shown in TABLE 2 and by dehydrating it under a reduced pressure at 100° C. for 6 hours was heated to 110° C. With maintaining the temperature, glycidol containing 1.68% of chlorohydrin as an impurity was supplied for 1 hour so that the Cl derived from chlorohydrin came to be equivalent to the first supplied K and an aging was carried out for 3 hours. After that, 3.64-fold amount of 96% KOH with respect to the amount of the first supplied KOH was supplied and was heated to 110° C., and it was dehydrated under a reduced pressure for 4 hours. Then, with maintaining the temperature, glycidol containing 1.68% of chlorohydrin as an impurity was supplied for 3 hours so that the concentration of the components derived from glycidol came to be 49%. After that, an aging was further carried out at 110° C. for 15 hours to obtain polyol A11.

Example A12

An alcoholate, which was obtained by supplying KOH so that the catalyst cation concentration came to be a (mol/OH) with respect to OH of the base polyol (I) shown in TABLE 2 and by dehydrating it under a reduced pressure at 100° C. for 6 hours, was heated to 110° C. With maintaining the temperature, glycidol containing 0.5% of chlorohydrin as an impurity was supplied for 4 hours so that the CI derived from chlorohydrin came to be equivalent to the first supplied K. After that, 4.85-fold amount of 96% KOH with respect to the amount of the first supplied KOH was supplied and was heated to 130° C., and it was dehydrated under a reduced pressure for 4 hours. Then, with maintaining the temperature, glycidol containing 0.5% of chlorohydrin as an impurity was supplied for 6.7 hours so that the concentration of the components derived from glycidol came to be 80%. After that, an aging was further carried out at 130° C. for 17 hours to obtain polyol A12.

Example A13

Polyol A6 was supplied to an autoclave and was heated to 120° C., and 5 parts of ethylene oxide with respect to 100 parts of the polyol was charged for 7.6 hours with maintaining 120° C. After that, the internal pressured reaction was carried out at 120° C. for 4.3 hours to obtain polyol A13.

Example A14

To a four-necked flask of 100 ml equipped with a thermometer, a stirrer, a nitrogen introduction tube and a monomer drip line, polyol I-1 as the base polyol (I) was charged. Then, it was heated to 100° C., and glycidol (produced by Wako Pure Chemical Industries, Ltd., for chemical use, the same applied hereinafter) as alkylene oxide (II) was charged using a proportioning pump at a speed so that the reaction temperature could be maintained at 100° C. In this regard, the mol ratio of base polyol (I) and alkylene oxide (II) was set to be 1/7. Also, the average functional group number calculated by the supplied composition was 10. After that, an aging was carried out at 100° C. for 5 hours to obtain polyol A14.

Example A15

Polyol A15 was obtained in the same manner as in A14 except that the mol ratio of base polyol (I) and glycidol that was alkylene oxide (II) was 1/21.

Comparative Examples A1 and A2

The base polyol (I) shown in TABLE 3 was evaluated without reacting glycidol,

Comparative Examples A3 to A5

PZN or MI was supplied so that the catalyst cation concentration came to be a (mol/OH) with respect to OH of the base polyol (I) shown in TABLE 3. After that, glycidol was added in the amount shown in TABLE 3 and the reaction was carried out at 130° C. for a time shown in TABLE 3 to obtain a polyol. The polyols of Comparative Examples A4 and A5 was divided into two layers.

<Production of Flexible Polyurethane Foam>

Examples A16 to A38 and Comparative Examples A6 to A15

First, using a raw material shown in TABLE 4 to TABLE 10, a resin premix was prepared.

Polyol B1 was produced as follows. To an alcoholate which was obtained by adding potassium hydroxide to glycerin in an amount of 10 mol % per hydroxyl group and by dehydrating it under a reduced pressure at 100° C. for 6 hours, an addition polymerization of propylene oxide was carried out in an autoclave at a reaction temperature of 110° C. under a maximum reaction pressure of 0.4 MPaG. Then, an addition polymerization of ethylene oxide was carried out at a reaction temperature of 100° C. under a maximum reaction pressure of 0.4 MPaG so that the ethylene oxide came to be 15% of the whole amount, to obtain a crude polyol. 1.02 equivalents of phosphoric acid with respect to potassium in this crude polyol and 5 parts of water with respect to 100 parts of the crude polyol were added, and it was neutralized at 90° C. for 1 hour. Then, it was dehydrated at 110° C. under a reduced pressure so that the water content came to be 500 ppm and the precipitated neutralized salt was filtered to obtain polyol B1 with a hydroxyl value of 28 mgKOH/g and a total unsaturation degree of 0.07 meq/g.

Polyol B2 was produced as follows. First, polyol B4 with a hydroxyl value of 34 mgKOH/g was obtained in the same manner as in above-mentioned polyol B1 except that ethylene oxide was reacted so that the ethylene oxide came to be 14% of the whole amount. This polyol B4 was supplied to a pressure-resistant autoclave of 1 liter equipped with a thermometer, a stirring apparatus, a pressure gauge and a liquid sending apparatus so that the autoclave was filled up with the polyol, and it was heated to 120° C. with stirring. Further, a mixture liquid of 79.4 parts of polyol B4, 1 part of 2,2'-azobisisobutyronitrile that is a radical polymerization initiator, and 16.5 parts of acrylonitrile and 4.1 parts styrene (acrylonitrile/styrene=80/20 mass ratio, total amount of acrylonitrile and styrene: 20.6 parts) was continuously charged to this autoclave under the conditions of a reaction temperature of 120° C., of a reaction pressure of 0.4 MPaG, and of a staying time of 50 minutes, to polymerize the acrylonitrile and the styrene in polyol B4. And, an initial fraction was removed so that a polymer came to be uniformly dispersed in a reaction liquid which was continuously exhausted from the outlet, to obtain the reaction liquid exhausted. This reaction liquid was continuously heated under a reduced pressure under the conditions of 120° C. and 0.7 kPaG or less, and an unreacted acrylonitrile, styrene and a decomposition material of the radical polymerization were removed to obtain polyol B2 with a hydroxyl value of 28 mgKOH/g. When the residual amount of acrylonitrile and styrene remaining in polyol B2 before heating under a reduced pressure was measured by gas chromatography, the content of the vinyl polymer contained in polyol B2 was 20%.

Polyol B3 was produced as follows. Polyol B4 was supplied to a pressure-resistant autoclave of 1 liter equipped with a thermometer, a stirring apparatus, a pressure gauge and a liquid sending apparatus so that the autoclave was filled up with the polyol, and it was heated to 120° C. with stirring. Further, a mixture liquid of 69.4 parts of polyol B4, 1 part of 2,2'-azobisisobutyronitrile that is a radical polymerization initiator, and 30.6 parts of acrylonitrile was continuously charged to this autoclave under the conditions of a reaction temperature of 120° C., of a reaction pressure of 0.4 MPaG, and of a staying time of 50 minutes, to polymerize the acrylonitrile in polyol B4. An initial fraction was removed so that a polymer came to be uniformly dispersed in a reaction liquid which was continuously exhausted from the outlet, to obtain the reaction liquid exhausted. This reaction liquid was continuously heated under a reduced pressure under the conditions of 120° C. and 0.7 kPaG or less, and an unreacted acrylonitrile and a decomposition material of the radical polymerization were removed to obtain polyol B3 with a hydroxyl value of 23 mgKOH/g. When the residual amount of acrylonitrile remaining in polyol B3 before heating under a reduced pressure was measured by gas chromatography, the content of the vinyl polymer contained in polyol B3 was 30%.

Cell opener-1 used was produced as follows. First, potassium hydroxide was added in an amount of 0.1 mol per 1 mol of hydroxyl group contained in glycerin and it was dehydrated under a reduced pressure at 100° C. for 6 hours. After that, an addition polymerization of 14% of ethylene oxide was carried out in an autoclave at a reaction temperature of 115° C. under a maximum reaction pressure of 0.4 MPaG. Then, an addition polymerization of 30% of propylene oxide and 56% of ethylene oxide was carried out at a reaction temperature of 115° C. under a maximum reaction pressure of 0.5 MPaG, and a neutralization, dehydration and filtration steps were carried out by the same operation as in polyol B1 to obtain cell opener-1. The hydroxyl value of this cell opener-1 was 50 mgKOH/g, and the content of ethylene oxide (EO) was 70% from the supplied ratio.

Crosslinker-1 used was produced as follows. First, potassium hydroxide was added in an amount of 0.37 mol per 1.2 mol of pentaerythritol and 1 mol of diglycerin and it was dehydrated under a reduced pressure at 100° C. for 6 hours. After that, an addition polymerization of 100% of ethylene oxide was carried out in an autoclave at a reaction temperature of 115° C. under a maximum reaction pressure of 0.4 MPaG. Then, a neutralization, dehydration and filtration were carried out in the same manner as in cell opener-1, and 25% of diethanolamine was mixed. The hydroxyl value of this crosslinker-1 was 840 mgKOH/g.

The foaming agent used was water, catalyst-1 used was MINICO TMDA (trade name) produced by Katsuzai-Chemical Corporation, catalyst-2 used was MINICO L-1020 (trade name) produced by Katsuzai-Chemical Corporation, surfactant-1 uses was SZ-1966 (trade name) produced by Dow Corning Toray Co., Ltd., surfactant-2 uses was L-5309 (trade name) produced by Momentive Performance Materials Japan limited liability company, surfactant-3 uses was SZ-1966 (trade name) produced by Dow Corning Toray Co., Ltd., surfactant-4 uses was DABCO DC-2525 (trade name) produced by Air Products Japan, Inc., and surfactant-5 uses was DABCO DC-6070 (trade name) produced by Air Products Japan, Inc.

And, a resin premix of these was mixed with an isocyanate compound (produced by Mitsui Chemicals, Inc., trade name: COSMONATE TM-20) in an NCO index of 1.00. It was promptly injected to a mold (inside size: 400 mm×400 mm×100 mm) at 63° C., and the lid was closed to foam it. The curing reaction proceeded for 6 minutes with keeping the mold temperature of 63° C. and the demolding from the mold was carried out to obtain a flexible polyurethane foam.

From the results shown in TABLE 4 to TABLE 10, it is found that the polyol (A) of each Example can maintain or improve the hardness of the flexible polyurethane foam and can maintain the ban rebound or the compression set that is an indicator of durability in a good balance.

TABLE 1

|  |  | Ex. A1 | Ex. A2 | Ex. A3 | Ex. A4 | Ex. A5 | Ex. A6 | Ex. A7 | Ex. A8 |
|---|---|---|---|---|---|---|---|---|---|
| Base Polyol (I) | f | 2 | 2 | 3 | 4 | 4 | 3 | 3 | 3 |
| | Calculated Mn | 3000 | 3000 | 5000 | 6600 | 6600 | 5000 | 5000 | 5000 |
| | Content of EO (wt %) | 20 | 20 | 15 | 15 | 15 | 14 | 14 | 14 |
| Alkylene Oxide (II) | Calculated Functional Group Number | 20 | 12.5 | 20 | 20 | 26.3 | 20 | 6.5 | 270 |
| | Glycidol (wt %) | 30.1 | 20 | 20.3 | 15.2 | 20 | 20 | 5 | 80 |
| | Ratio of Glycidol in Alkylene Oxide (II) (wt %) | 100 | 100 | 100 | 100 | 100 | 100 | 100 | 100 |
| | AO/Glycidol Ratio in Polyol | 75.3/24.7 | 84.0/16.0 | 83.8/16.2 | 88.0/12.0 | 84.0/16.0 | 84.2/15.8 | 96.2/3.8 | 24.7/75.3 |
| Catalyst | | PZN | PZN | PZN | PZN | PZN | PZN | PZN | PZN |
| Reaction Temperature | | 130 | 130 | 130 | 130 | 130 | 110 | 110 | 110 |
| Charging Time of Glycidol | | 2 | 2 | 2 | 2 | 2 | 2 | 0.5 | 8 |
| Aging Time | | 4 | 4 | 4 | 4 | 4.4 | 8 | 6.5 | 20 |
| Analyzed Values | OHV(mgKOH/g) | 238.7 | 169.3 | 171.3 | 132.6 | 166.8 | 174.2 | 68.2 | 602.1 |
| | Viscosity (mPa·s/25° C.) | 1660 | 1180 | 1660 | 1610 | 1880 | 1990 | 1150 | 200000 |
| | Mw/Mn | 12.3 | 11.5 | 10.9 | 14.6 | 9.6 | 10.3 | 11.0 | 12.0 |
| | High Molecular Weight Side (S2) | 29.00 | 22.34 | 21.03 | 19.90 | 19.84 | 6.69 | 1.10 | 0.00 |
| | Low Molecular Weight Side (S3) | 5.00 | 4.83 | 12.15 | 7.07 | 8.18 | 21.72 | 6.10 | 79.20 |
| | S1 | 66.00 | 72.83 | 66.82 | 73.03 | 71.98 | 71.59 | 92.80 | 20.80 |
| | S1/S2 | 69.5/30.5 | 76.5/23.5 | 76.1/23.9 | 78.6/21.4 | 78.4/21.6 | 91.5/8.5 | 98.8/1.2 | 100/0 |
| Charging Speed | α: Concentration of Catalyst Cation(mol/Initiator OH) | 0.0015 | 0.0013 | 0.0014 | 0.0013 | 0.0014 | 0.0018 | 0.0018 | 0.0018 |
| | β: Concentration of Initiator OH(mol/kg) | 0.67 | 0.67 | 0.60 | 0.61 | 0.61 | 0.60 | 0.60 | 0.60 |
| | γ: Charging Speed of Glycidol (mol/Hr·kg) | 3.00 | 1.69 | 1.72 | 1.21 | 1.69 | 1.72 | 1.42 | 13.51 |
| | γ/(α * β) | 3000 | 1950 | 2048 | 1536 | 1992 | 1593 | 1315 | 12509 |

TABLE 2

|  |  | Ex. A9 | Ex. A10 | Ex. A11 | Ex. A12 | Ex. A13 | Ex. A14 | Ex. A15 |
|---|---|---|---|---|---|---|---|---|
| Base Polyol (I) | f | 3 | 3 | 3 | 3 | 3 | 3 | 3 |
|  | Calculated Mn | 6000 | 6000 | 6000 | 6000 | 5000 | 5000 | 5000 |
|  | Content of EO (wt %) | 15 | 15 | 15 | 15 | 14 | 14 | 14 |
| Alkylene Oxide (II) | Calculated Functional Group Number | 23 | 51 | 51 | 328 | 20 | 10 | 24 |
|  | Glycidol (wt %) | 20 | 49 | 49 | 80 | 19.2 | 9.5 | 23.7 |
|  | Ratio of Glycidol in Alkylene Oxide (II) (wt %) | 100 | 100 | 100 | 100 | 80.9 | 100 | 100 |
|  | AO/Glycidol Ratio in Polyol | 84.1/15.9 | 58.3/41.7 | 58.3/41.7 | 24.8/75.2 | 85.1/14.9 | 92.7/7.3 | 84.2/15.8 |
| Catalyst |  | K | K | K | K | PZN | PZN | PZN |
| Reaction Temperature |  | 130 | 110 | 110 | 110⇒130 | 120 | 100 | 100 |
| Charging Time of Glycidol |  | 2 | 4 | 4※ | 4⇒8 | 7.5 | 2 | 2 |
| Aging Time |  | 6.5 | 30 | 15 | 17 | 4 | 5 | 5 |
| Analyzed Values | OHV(mgKOH/g) | 166.2 | 356.4 | 361.2 | 563.2 | 158.2 | 102.9 | 178 |
|  | Viscosity (mPa·s/25° C.) | 3240 | 10300 | 9410 | 200000 | 1880 | 1240 | 1800 |
|  | Mw/Mn | 25.7 | 13.9 | 14.4 | 378.0 | 28.4 | 15.6 | 10.3 |
|  | High Molecular Weight Side (S2) | 22.69 | 42.98 | 45.76 | 57.40 | 23.13 | 2.94 | 9.21 |
|  | Low Molecular Weight Side (S3) | 8.48 | 8.57 | 5.36 | 20.00 | 11.63 | 9.80 | 20.34 |
|  | S1 | 68.83 | 48.46 | 48.88 | 22.60 | 65.24 | 87.26 | 70.45 |
|  | S1/S2 | 75.2/24.8 | 53.0/47.0 | 51.6/48.4 | 28.3/71.7 | 73.8/26.2 | 96.7/3.3 | 88.4/11.6 |
| Charging Speed | α: Concentration of Catalyst Cation(mol/Initiator OH) | 0.0829 | 0.0829 | 0.0829 | 0.0829 | 0.0018 | 0.0018 | 0.0018 |
|  | β: Concentration of Initiator OH(mol/kg) | 0.50 | 0.50 | 0.50 | 0.50 | 0.60 | 0.60 | 0.60 |
|  | γ: Charging Speed of Glycidol (mol/Hr·kg) | 1.66 | 3.18 | 3.18 | 3.18 | 1.72 | 1.41 | 2.04 |
|  | γ/(α * β) | 40 | 77 | 77 | 77 | 1593 | 1306 | 1889 |

※The charging speeds in the first 1 Hr and in the following 3 Hr are different.

TABLE 3

|  |  | Comp. Ex. A1 | Comp. Ex. A2 | Comp. Ex. A3 | Comp. Ex. A4 | Comp. Ex. A5 |
|---|---|---|---|---|---|---|
| Base Polyol (I) | f | 3 | 3 | 3 | 3 | 3 |
|  | Calculated Mn | 5000 | 6000 | 92 | 6000 | 6000 |
|  | Content of EO (wt %) | 14 | 15 | 0 | 15 | 15 |
| Alkylene Oxide (II) | Calculated Functional Group Number | 3 | 3 | 20 | 23 | 23 |
|  | Glycidol (wt %) | 0 | 0 | 41.3 | 20 | 20 |
|  | Ratio of Glycidol in Alkylene Oxide (II) (wt %) | — | — | 42.7 | 100 | 100 |
|  | AO/Glycidol Ratio in Polyol | 100/0 | 100/0 | 69.6/30.4 | 84.1/15.9 | 84.1/15.9 |
| Catalyst |  | PZN | K | PZN | KCl | KCl |
| Reaction Temperature |  | — | — | 120 | 130 | 130 |
| Charging Time of Glycidol |  | — | — | 4 | at once | at once |
| Aging Time |  | — | — | 6 | 6.5 | 17 |
| Analyzed Values | OHV(mgKOH/g) | 34 | 28 | 382 | 167.3 | 165.8 |
|  | Viscosity (mPa·s/25° C.) | 900 | 1200 | 6600 | unmeasurable | unmeasurable |
|  | Mw/Mn | 1.4 | 1.7 | 2.1 | 3.3 | 2.9 |
|  | High Molecular Weight Side (S2) | 0.00 | 0.00 | 0.00 | 0.00 | 0.00 |
|  | Low Molecular Weight Side (S3) | 0.87 | 7.73 | 0.00 | 15.89 | 12.98 |
|  | S1 | 99.13 | 92.27 | 100.00 | 84.11 | 87.02 |
|  | S1/S2 | 100/0 | 100/0 | 100/0 | 100/0 | 100/0 |
| Charging Speed | α: Concentration of Catalyst Cation(mol/Initiator OH) | 0.0018 | 0.0829 | 0.0028 | 0.0829 | 0.0083 |
|  | β: Concentration of Initiator OH(mol/kg) | 0.60 | 0.50 | 32.61 | 0.50 | 0.50 |
|  | γ: Charging Speed of Glycidol (mol/Hr·kg) | — | — | 184.50 | at once | at once |
|  | γ/(α * β) |  |  | 2050 |  |  |

TABLE 4

|  | Ex. A16 | Ex. A17 | Ex. A18 | Ex. A19 | Ex. A20 | Comp. Ex. A6 |
|---|---|---|---|---|---|---|
| Polyol B1 | 60 | 60 | 60 | 60 | 60 | 70 |
| Polyol B3 | 30 | 30 | 30 | 30 | 30 | 30 |
| Polyol (Ex. A1) | 10 |  |  |  |  |  |
| Polyol (Ex. A2) |  | 10 |  |  |  |  |
| Polyol (Ex. A3) |  |  | 10 |  |  |  |
| Polyol (Ex. A4) |  |  |  | 10 |  |  |
| Polyol (Ex. A5) |  |  |  |  | 10 |  |
| Crosslinker-1 | 3.0 | 3.0 | 3.0 | 3.0 | 3.0 | 3.0 |
| H2O | 4.1 | 4.1 | 4.1 | 4.1 | 4.1 | 4.1 |
| Catalyst-1 | 0.1 | 0.1 | 0.1 | 0.1 | 0.1 | 0.1 |
| Catalyst-2 | 0.4 | 0.4 | 0.4 | 0.4 | 0.4 | 0.4 |
| Surfactant-3 | 0.6 | 0.6 | 0.6 | 0.6 | 0.6 | 0.6 |
| TOTAL | 108.2 | 108.2 | 108.2 | 108.2 | 108.2 | 108.2 |

TABLE 4-continued

|  | Ex. A16 | Ex. A17 | Ex. A18 | Ex. A19 | Ex. A20 | Comp. Ex. A6 |
|---|---|---|---|---|---|---|
| Mass % of Polyol A with respect to 100 of Polyol B | 11.1 | 11.1 | 11.1 | 11.1 | 11.1 | 0.0 |
| Density: Core (kg/m3) | 37.2 | 37.2 | 37.1 | 36.9 | 37.2 | 37.5 |
| 25% ILD (N/314 cm2) | 211 | 196 | 189 | 184 | 192 | 160 |
| Tensile Strength (kPa) | 151 | 139 | 141 | 121 | 124 | 145 |
| Elongation (%) | 94 | 94 | 98 | 93 | 91 | 113 |
| Tear Strength (N/cm) | 4.6 | 5.1 | 4.9 | 4.5 | 5.2 | 4.8 |
| 50% Wet Set (%) | 13.0 | 13.2 | 13.2 | 13.1 | 13.5 | 14.7 |
| Ball Rebound: Core (%) | 66 | 67 | 67 | 69 | 68 | 69 |

TABLE 5

|  | Ex. A21 | Ex. A22 | Ex. A23 | Comp. Ex. A7 | Comp. Ex. A8 | Comp. Ex. A9 |
|---|---|---|---|---|---|---|
| Polyol B1 | 60 | 66 | 66 | 50 | 70 | 66 |
| Polyol B3 | 30 | 30 | 30 | 50 | 30 | 30 |
| Polyol (Ex. A9) | 10 |  |  |  |  |  |
| Polyol (Ex. A10) |  | 4 |  |  |  |  |
| Polyol (Ex. A11) |  |  | 4 |  |  |  |
| Polyol (Comp. Ex. A4) |  |  |  |  |  | 4 |
| Cell Opener-1 |  |  |  | 1 |  |  |
| Crosslinker-1 | 1.5 | 1.5 | 1.5 | 1.5 | 1.5 | 1.5 |
| H2O | 4.1 | 4.1 | 4.1 | 4.1 | 4.1 | 4.1 |
| Catalyst-1 | 0.1 | 0.1 | 0.1 | 0.1 | 0.1 | 0.1 |
| Catalyst-2 | 0.4 | 0.4 | 0.4 | 0.4 | 0.4 | 0.4 |
| Surfactant-3 | 0.6 | 0.6 | 0.6 |  | 0.6 | 0.6 |
| Surfactant-4 |  |  |  | 0.2 |  |  |
| Surfactant-5 |  |  |  | 0.8 |  |  |
| TOTAL | 106.7 | 106.7 | 106.7 | 108.1 | 106.7 | 106.7 |
| Mass % of Polyol A with respect to 100 of Polyol B | 11.1 | 4.2 | 4.2 | 0.0 | 0.0 | 4.2 |
| Density: Core (kg/m3) | 36.9 | 37.2 | 37.2 | 37.1 | 37.0 | The polyol was separated and a foam body was not obtained. |
| 25% ILD (N/314 cm2) | 197 | 187 | 185 | 196 | 162 |  |
| Tensile Strength (kPa) | 182 | 166 | 150 | 200 | 173 |  |
| Elongation (%) | 114 | 110 | 100 | 120 | 124 |  |
| Tear Strength (N/cm) | 5.2 | 5.3 | 5.2 | 6.8 | 6.5 |  |
| 50% Wet Set (%) | 18.4 | 21.2 | 17.6 | 23.6 | 25.9 |  |
| Ball Rebound: Core (%) | 68 | 67 | 67 | 65 | 66 |  |

TABLE 6

|  | Ex. A24 | Ex. A25 | Ex. A26 | Ex. A27 | Comp. Ex. A10 |
|---|---|---|---|---|---|
| Polyol B1 | 66 | 30 | 67.5 | 67.5 | 70 |
| Polyol B3 | 30 | 30 | 30 | 30 | 30 |
| Polyol (Ex. A11) | 4 |  |  |  |  |
| Polyol (Ex. A7) |  | 40 |  |  |  |
| Polyol (Ex. A12) |  |  | 2.5 |  |  |
| Polyol (Ex. A8) |  |  |  | 2.5 |  |
| Crosslinker-1 | 1.5 | 1.5 | 1.5 | 1.5 | 1.5 |
| H2O | 4.1 | 4.1 | 4.1 | 4.1 | 4.1 |
| Catalyst-1 | 0.1 | 0.1 | 0.1 | 0.1 | 0.1 |
| Catalyst-2 | 0.4 | 0.4 | 0.4 | 0.4 | 0.4 |
| Surfactant-3 | 0.6 | 0.6 | 0.6 | 0.6 | 0.6 |
| TOTAL | 106.7 | 106.7 | 106.7 | 106.7 | 106.7 |

TABLE 6-continued

|  | Ex. A24 | Ex. A25 | Ex. A26 | Ex. A27 | Comp. Ex. A10 |
|---|---|---|---|---|---|
| Mass % of Polyol A with respect to 100 of Polyol B | 4.2 | 66.7 | 2.6 | 2.6 | 0.0 |
| Density: Core (kg/m3) | 37.2 | 38.2 | 37.4 | 37.8 | 40.1 |
| 25% ILD (N/314 cm2) | 185 | 193 | 181 | 165 | 158 |
| Tensile Strength (kPa) | 150 | 161 | 165 | 152 | 162 |
| Elongation (%) | 100 | 94 | 109 | 101 | 119 |
| Tear Strength (N/cm) | 5.2 | 6.3 | 6.2 | 6.0 | 7.2 |
| 50% Wet Set (%) | 17.6 | 16.9 | 18.1 | 14.8 | 21.8 |
| Ball Rebound: Core (%) | 67 | 66 | 66 | 67 | 66 |

TABLE 7

|  | Ex. A28 | Ex. A29 | Comp. Ex. A11 |
|---|---|---|---|
| Polyol B1 | 60 | 59.5 | 70 |
| Polyol B3 | 30 | 30 | 30 |
| Polyol (Ex. A6) | 10 |  |  |
| Polyol (Ex. A13) |  | 10.5 |  |
| Crosslinker-1 | 1.5 | 1.5 | 1.5 |
| H2O | 4.1 | 4.1 | 4.1 |
| Catalyst-1 | 0.1 | 0.1 | 0.1 |
| Catalyst-2 | 0.4 | 0.4 | 0.4 |
| Surfactant-3 | 0.6 | 0.6 | 0.6 |
| TOTAL | 106.7 | 106.7 | 106.7 |
| Mass % of Polyol A with respect to 100 of Polyol B | 11.1 | 11.7 | 0.0 |
| Density: Core (kg/m3) | 38.2 | 40.0 | 40.1 |
| 25% ILD (N/314 cm2) | 189 | 183 | 158 |
| Tensile Strength (kPa) | 163 | 159 | 162 |
| Elongation (%) | 98 | 105 | 119 |
| Tear Strength (N/cm) | 5.4 | 5.1 | 7.2 |
| 50% Wet Set (%) | 16.9 | 16.5 | 21.8 |
| Ball Rebound: Core (%) | 65 | 66 | 66 |

TABLE 8

|  | Ex. A30 | Ex. A31 | Ex. A32 | Ex. A33 | Comp. Ex. A12 |
|---|---|---|---|---|---|
| Polyol B1 | 60 | 45 | 66 | 60 | 70 |
| Polyol B3 | 30 | 30 | 30 | 30 | 30 |
| Polyol (Ex. A6) | 10 | 25 |  |  |  |
| Polyol (Ex. A10) |  |  | 4 | 10 |  |
| Crosslinker-1 | 1.5 | 1.5 | 1.5 | 1.5 | 1.5 |
| H2O | 4.1 | 4.1 | 4.1 | 4.1 | 4.1 |
| Catalyst-1 | 0.1 | 0.1 | 0.1 | 0.1 | 0.1 |
| Catalyst-2 | 0.4 | 0.4 | 0.4 | 0.4 | 0.4 |
| Surfactant-3 | 0.6 | 1.0 | 0.6 | 1.0 | 0.6 |
| TOTAL | 106.7 | 107.1 | 106.7 | 107.1 | 106.7 |
| Concentration of Glycidol Body in Polyol | 2.0 | 5.0 | 2.0 | 5.0 | 0.0 |
| Density: Core (kg/m3) | 37.2 | 36.8 | 37.3 | 36.7 | 40.1 |
| 25% ILD (N/314 cm2) | 183 | 209 | 194 | 217 | 158 |
| Tensile Strength (kPa) | 170 | 181 | 160 | 146 | 162 |
| Elongation (%) | 111 | 99 | 106 | 91 | 119 |
| Tear Strength (N/cm) | 5.9 | 5.8 | 6.1 | 4.5 | 7.2 |
| 50% Wet Set (%) | 16.5 | 15.2 | 18.8 | 18.1 | 21.8 |
| Ball Rebound: Core (%) | 66 | 65 | 66 | 65 | 66 |

TABLE 9

|  | Ex. A34 | Ex. A35 | Ex. A36 | Comp. Ex. A13 | Comp. Ex. A14 |
|---|---|---|---|---|---|
| Polyol B1 | 30 | 45 | 60 | 30 | 30 |
| Polyol B2 | 60 | 45 | 30 | 70 | 70 |
| Polyol (Ex. A15) | 10 | 10 | 10 |  |  |
| Polyol (Comp. Ex. A3) |  |  |  |  | 2 |
| Cell Opener-1 | 1.0 | 1.0 | 1.0 | 1.0 | 1.0 |
| Crosslinker-1 | 2.0 | 2.0 | 2.0 | 2.0 | 2.0 |
| H2O | 3.5 | 3.5 | 3.5 | 3.5 | 3.5 |
| Catalyst-1 | 0.1 | 0.1 | 0.1 | 0.1 | 0.1 |
| Catalyst-2 | 0.4 | 0.4 | 0.4 | 0.4 | 0.4 |
| Surfactant-1 |  |  |  |  | 1.0 |
| Surtactant-2 | 1.0 | 1.0 | 1.0 | 1.0 |  |
| TOTAL | 108.0 | 108.0 | 108.0 | 108.0 | 110.0 |
| Mass % of Polyol A with respect to 100 of Polyol B | 11.1 | 11.1 | 11.1 | 0.0 | 0.0 |
| Density: Core (kg/m3) | 46.9 | 47.1 | 46.4 | 44.5 | 45.0 |
| 25% ILD (N/314 cm2) | 243 | 220 | 192 | 212 | 174 |
| Tensile Strength (kPa) | 190 | 160 | 153 | 209 | 181 |
| Elongation (%) | 103 | 101 | 105 | 112 | 111 |
| Tear Strength (N/cm) | 6.2 | 5.5 | 4.9 | 7.2 | 6.6 |
| 50% Wet Set (%) | 15.8 | 12.0 | 11.3 | 16.9 | 16.5 |
| Ball Rebound: Core (%) | 69 | 70 | 73 | 67 | 67 |

TABLE 10

|  | Ex. A37 | Ex. A38 | Comp. Ex. A15 |
|---|---|---|---|
| Polyol B1 | 50 | 65 | 50 |
| Polyol B3 | 30 | 15 | 50 |
| Polyol (Ex. A15) |  | 20 |  |
| Polyol (Ex. A14) | 20 |  |  |
| Cell Opener-1 | 2 | 1 | 1 |
| Crosslinker-1 | 2 | 2 | 3 |
| H2O | 4.1 | 4.1 | 4.1 |
| Catalyst-1 | 0.05 | 0.05 | 0.1 |
| Catalyst-2 | 0.45 | 0.45 | 0.4 |
| Surfactant-3 | 0.7 | 0.7 |  |
| Surfactant-4 |  |  | 0.2 |
| Surfactant-5 |  |  | 0.8 |
| TOTAL | 109.3 | 108.3 | 109.6 |
| Mass % of Polyol A with respect to 100 of Polyol B | 25 | 25 | 0 |
| Density: Core (kg/m3) | 37.8 | 38.0 | 37.5 |
| 25% ILD (N/314 cm2) | 181 | 176 | 185 |
| Tensile Strength (kPa) | 92 | 88 | 132 |
| Elongation (%) | 80 | 88 | 104 |
| Tear Strength (N/cm) | 4.0 | 3.7 | 5.2 |
| 50% Wet Set (%) | 15.1 | 12.1 | 17.1 |
| Ball Rebound: Core (%) | 70 | 70 | 67 |

Next, Example a of the second invention is described,

Example a1

To an alcoholate obtained by adding 0.005 mol of PZN with respect to 1 mol of glycerin and by dehydrating it under a reduced pressure at 100° C. for 6 hours, an addition polymerization of propylene oxide was carried out in an autoclave at a reaction temperature of 90° C. under a maximum reaction pressure of 0.4 MPaG. Then, an addition polymerization of ethylene oxide was carried out at a reaction temperature of 100° C. under a maximum reaction pressure of 0.4 MPaG so that ethylene oxide in the whole came to be 14%, to obtain polyol i-1, The total unsaturation degree of this polyol i-1 was 0.020 meq/g, the hydroxyl value was 34 mgKOH/g, and the residual catalyst concentration was 0.18 mol %/active hydrogen.

To a four-necked flask of 100 ml equipped with a thermometer, a stirrer, a nitrogen introduction tube and a monomer drip line, 76.0 parts of polyol i-1 as active hydrogen compound (i) was charged. Then, it was heated to 100° C., and 24.1 parts of glycidol (produced by Wako Pure Chemical Industries, Ltd., for chemical use, the same applied hereinafter) as alkylene oxide (ii) was charged using a proportioning pump at a speed so that the reaction temperature could be maintained at 100° C. In this alkylene oxide (ii), the mol ratio of glycidol and alkylene oxide except for glycidol was 100/0, and the mol ratio of active hydrogen compound (i) and alkylene oxide (ii) was 1/21, and the average functional group number calculated by the supplied composition was 24. After that, an aging was carried out at 100° C. for 5 hours to obtain polyol a1.

Examples a2 to a11

Polyols a2 to a11 were obtained by changing active hydrogen compound (i) and alkylene oxide (ii) as shown in TABLE 11.

Example a2 is an example which is the same as Example A14 of the first invention. In Examples a3 to a6, a7 and a9, the whole amount of the prepared glycerin and the prepared catalyst were charged to the four-necked flask of 100 ml and it was dehydrated under a reduced pressure at 100° C. for 5 hours, and glycidol was then charged. After that, the reaction was carried out in the same operation as that of polyol a1. Also, in the production in Examples a1 to a6, a phosphazenium salt compound was used as a basic compound, but was used for the production of a flexible polyurethane foam without carrying out the decatalyst step.

Example a8 is an example in which glycidol uses as alkylene oxide (ii) was also used as active hydrogen compound (i). Also, Example a10 is an example in which alkylene oxide (ii) and propylene oxide (PO) were copolymerized, and Example a11 is an example in which alkylene oxide (ii) and ethylene oxide (EO) were copolymerized.

Comparative Examples a1 to a4

As shown in TABLE 11, properties of polyglycerins 06, 10 and X produced by Daicel Corporation are shown for comparison. These have a primary hydroxylate ratio that is too high.

<Production of Flexible Polyurethane Foam>

Examples a12 to a25 and Comparative Examples a5 to a12

First, using a raw material shown in TABLE 12 to TABLE 14, a resin premix was prepared. Each component used such as the cell opener was the same as that of Example A, Polyols b1, b2 and b3 used were the same as polyols B1, B2 and B3. Polyol a4 is the same as that of Comparative Example A3.

And, a resin premix of these was mixed with an isocyanate compound (produced by Mitsui Chemicals, Inc., trade name: COSMONATE TM-20) in an NCO index of 1.00. It was promptly injected to a mold (inside size: 400 mm 400 mm×100 mm) at 60° C., and the lid was closed to foam it. The curing reaction proceeded for 8 minutes with keeping the mold temperature of 60° C. and the demolding from the mold was carried out to obtain a flexible polyurethane foam.

From the results shown in TABLE 12 to TABLE 14, it is found that the polyol (a) of each Example can improve the hardness of the flexible polyurethane foam without lowering the durability and the ball rebound. In particular, when compared to each Comparative Example where the primary OH-ate ratio is larger than 60%, the effect of improving the hardness developing and the Wet Set is large in each Example. Also, it is found that the effect of improving the hardness and the Wet Set is large if the primary OH-ate ratio is 25 to 60% even if EO and PO are copolymerized.

On the other hand, the flexible polyurethane polyol of Comparative Example a5 is known as a prior art. Herein, although the used amount of the polymer dispersed polyol as an polyol is adjusted to improve the hardness of the flexible polyurethane foam, the balance with the 50% Wet Set and the ball rebound core is not sufficient. Also, Comparative Examples a9 to a11 are a prior art which intends to improve the hardness by a crosslinker described in BACKGROUND ART. Herein, it is found not only that the foam hardness is not largely improved, but also that 50% Wet Set was largely reduced.

TABLE 11

|  |  | Ex. a1 | Ex. a2 | Ex. a3 | Ex. a4 | Ex. a5 | Ex. a6 | Ex. a7 | Ex. a8 |
| --- | --- | --- | --- | --- | --- | --- | --- | --- | --- |
| Active Hydrogen Compound (I) | Kind | Polyol i-1 | Polyol i-1 | Glycerin | Glycerin | Glycerin | Glycerin | Glycerin | non |
|  | Average Functional Group Number of Active Hydrogen Compound | 3 | 3 | 3 | 3 | 3 | 3 | 3 | 0 |
| Alkylene Oxide (ii) | Added Mol Number of Glycidol with respect to Active Hydrogen Compound (x) | 21 | 7 | 5 | 30 | 154 | 671 | 9 | ※1 |
|  | Alkylene Oxide other than Glycidol | — | — | — | — | — | — | — | — |
|  | Added Mol Number of the above (y) | — | — | — | — | — | — | — | — |
| (x)/(x) + (y) (mol %) |  | 100 | 100 | 100 | 100 | 100 | 100 | 100 | 100 |
| Average Number of Functional Groups |  | 24 | 10 | 8 | 33 | 157 | 674 | 12 | ※2 |
| OHV(mgKOH/g) |  | 178 | 103 | 962 | 795 | 738 | 735 | 862 | 743 |
| Viscosity (mPa·s/25° C.) |  | 1,800 | 1,200 | no flowability | no flowability | no flowability | no flowability | no flowability | no flowability |
| Molecular Weight Mp |  | 7,080 | 6,880 | 440 | 1,580 | 9,060 | 23,000 | 752 | 956 |
| Molecular Weight Mn |  | 910 | 1,490 | 140 | 380 | 940 | 600 | 248 | 256 |
| Molecular Weight Mw |  | 8,230 | 7,460 | 470 | 1,480 | 7,340 | 15,500 | 769 | 1,240 |
| Molecular Weight Distribution Mw/Mn |  | 9.0 | 5.0 | 3.4 | 3.9 | 7.8 | 25.8 | 3.1 | 4.8 |
| Average Number of Functional Groups Calculated by HOV and Mp |  | 22.5 | 12.6 | 8 | 22 | 119 | 301 | 12 | 13 |
| Appearance |  | white liquid | white liquid |  |  |  | pale yellow transparent liquid | slightly turbid liquid | slightly turbid liquid |
| Primary OH-ate Ratio (%) |  | 50.8 | 56.4 | 48.8 | 46.4 | 46.4 | 46.2 | 47.4 | 45.5 |

|  |  | Ex. a9 | Ex. a10 | Ex. a11 | Comp. Ex. a1 | Comp. Ex. a2 | Comp. Ex. a3 | Comp. Ex. a4 |
| --- | --- | --- | --- | --- | --- | --- | --- | --- |
| Active Hydrogen Compound (I) | Kind | Glycerin | Glycerin | Glycerin | Polyglycerin 08 | Polyglycerin 10 | Polyglycerin X | Glycerin |
|  | Average Functional Group Number of Active Hydrogen Compound | 3 | 3 | 3 | 3 | 3 | 3 | 3 |
| Alkylene Oxide (ii) | Added Mol Number of Glycidol with respect to Active Hydrogen Compound (x) | 17 | 17 | 17 | — | — | — | 17 |
|  | Alkylene Oxide other than Glycidol | — | PO | EO |  |  |  | EO |
|  | Added Mol Number of the above (y) | — | 8.8 | 11.2 | — | — | — | 39.0 |
| (x)/(x) + (y) (mol %) |  | 100 | 65.9 | 60.3 | — | — | — | 30.4 |
| Average Number of Functional Groups |  | 20 | 20 | 20 | 8 | 12 | 22 | 20 |
| OHV(mgKOH/g) |  | 815 | 626 | 649 | 951 | 867 | 756 | 382 |
| Viscosity (mPa·s/25° C.) |  | no flowability | no flowability | 94,800 | no flowability | no flowability | no flowability | 6,600 |
| Molecular Weight Mp |  | 1,250 | 1,930 | 1,690 | 530 | 830 | 3,140 | 2,860 |
| Molecular Weight Mn |  | 421 | 332 | 598 | 200 | 280 | 580 | 1,290 |
| Molecular Weight Mw |  | 1,210 | 1,750 | 1,650 | 530 | 850 | 3,210 | 2,610 |
| Molecular Weight Distribution Mw/Mn |  | 2.9 | 5.3 | 2.8 | 2.7 | 3.0 | 5.5 | 2.0 |
| Average Number of Functional Groups Calculated by HOV and Mp |  | 18 | 22 | 20 | 9 | 13 | 42 | 20 |
| Appearance |  | pale yellow transparent | slightly turbid liquid | slightly turbid liquid | white | transparent | transparent viscous liquid | pale yellow transparent liquid |
| Primary OH-ate Ratio (%) |  | 46.7 | 29.2 | 59.3 | 64.8 | 64.7 | 65.1 | 82.7 |

Average functional group number is the number of the active hydrogen group in the molecule, and is represented by an integer value by rounding off the number.
※1 The value cannot be calculated because glycidol per se is (i).
※2 It cannot be calculated because there is not a mol ratio of (i)/glycidol.

TABLE 12

|  | Ex. a12 | Ex. a13 | Ex. a14 | Comp. Ex. a5 | Comp. Ex. a6 |
|---|---|---|---|---|---|
| Polyol b1 | 30 | 45 | 60 | 30 | 30 |
| Polyol b2 | 60 | 45 | 30 | 70 | 70 |
| Polyol (Ex. a1) | 10 | 10 | 10 |  |  |
| Polyol (Comp. Ex. a4) |  |  |  |  | 2 |
| Cell Opener-1 | 1.0 | 1.0 | 1.0 | 1.0 | 1.0 |
| Crosslinker-1 | 2.0 | 2.0 | 2.0 | 2.0 | 2.0 |
| H2O | 3.5 | 3.5 | 3.5 | 3.5 | 3.5 |
| Catalyst-1 | 0.1 | 0.1 | 0.1 | 0.1 | 0.1 |
| Catalyst-2 | 0.4 | 0.4 | 0.4 | 0.4 | 0.4 |
| Surfactant-1 |  |  |  |  | 1.0 |
| Surtactant-2 | 1.0 | 1.0 | 1.0 | 1.0 |  |
| TOTAL | 108.0 | 108.0 | 108.0 | 108.0 | 110.0 |
| Mass % of Polyol a with respect to 100 of Polyol b | 11.1 | 11.1 | 11.1 | 0.0 | 0.0 |
| Density: Core (kg/m3) | 46.9 | 47.1 | 46.4 | 44.5 | 45.0 |
| 25% ILD (N/314 cm2) | 243 | 220 | 192 | 212 | 174 |
| Tensile Strength (kPa) | 190 | 160 | 153 | 209 | 181 |
| Elongation (%) | 103 | 101 | 105 | 112 | 111 |
| Tear Strength (N/cm) | 6.2 | 5.5 | 4.9 | 7.2 | 6.6 |
| 50% Wet Set (%) | 15.8 | 12.0 | 11.3 | 16.9 | 16.5 |
| Ball Rebound: Core (%) | 69 | 70 | 73 | 67 | 67 |

TABLE 13

|  | Ex. a15 | Ex. a16 | Comp Ex. a7 |
|---|---|---|---|
| Polyol b1 | 50 | 65 | 50 |
| Polyol b3 | 30 | 15 | 50 |
| Polyol (Ex. a1) |  | 20 |  |
| Polyol (Ex. a2) | 20 |  |  |
| Cell Opener-1 | 2 | 1 | 1 |
| Crosslinker-1 | 2 | 2 | 3 |
| H2O | 4.1 | 4.1 | 4.1 |
| Catalyst-1 | 0.05 | 0.05 | 0.1 |
| Catalyst-2 | 0.45 | 0.45 | 0.4 |
| Surfactant-3 | 0.7 | 0.7 |  |
| Surfactant-4 |  |  | 0.2 |
| Surfactant-5 |  |  | 0.8 |
| TOTAL | 109.3 | 108.3 | 109.6 |
| Mass % of Polyol a with respect to 100 of Polyol b | 25 | 25 | 0 |
| Density: Core (kg/m3) | 37.8 | 38.0 | 37.5 |
| 25% ILD (N/314 cm2) | 181 | 176 | 185 |
| Tensile Strength (kPa) | 92 | 88 | 132 |
| Elongation (%) | 80 | 88 | 104 |
| Tear Strength (N/cm) | 4.0 | 3.7 | 5.2 |
| 50% Wet Set (%) | 15.1 | 12.1 | 17.1 |
| Ball Rebound: Core (%) | 70 | 70 | 67 |

TABLE 14

|  | Ex. a17 | Ex. a18 | Ex. a19 | Ex. a20 | Ex. a21 | Ex. a22 | Ex. a23 | Ex. a24 | Ex. a25 | Comp. Ex. a8 | Comp. Ex. a9 | Comp. Ex. a10 | Comp. Ex. a11 | Comp. Ex. a12 |
|---|---|---|---|---|---|---|---|---|---|---|---|---|---|---|
| Polyol b1 | 50 | 50 | 50 | 50 | 70 | 70 | 70 | 70 | 70 | 50 | 50 | 50 | 50 | 70 |
| Polyol b3 | 50 | 50 | 50 | 50 | 30 | 30 | 30 | 30 | 30 | 50 | 50 | 50 | 50 | 30 |
| Polyol (Ex. a3) | 4 |  |  |  |  |  |  |  |  |  |  |  |  |  |
| Polyol (Ex. a4) |  | 4 |  |  |  |  |  |  |  |  |  |  |  |  |
| Polyol (Ex. a5) |  |  | 4 |  |  |  |  |  |  |  |  |  |  |  |
| Polyol (Ex. a6) |  |  |  | 4 |  |  |  |  |  |  |  |  |  |  |
| Polyol (Ex. a7) |  |  |  |  | 2 |  |  |  |  |  |  |  |  |  |
| Polyol (Ex. a8) |  |  |  |  |  | 2 |  |  |  |  |  |  |  |  |
| Polyol (Ex. a9) |  |  |  |  |  |  | 2 |  |  |  |  |  |  |  |
| Polyol (Ex. a10) |  |  |  |  |  |  |  | 2 |  |  |  |  |  |  |
| Polyol (Ex. a11) |  |  |  |  |  |  |  |  | 2 |  |  |  |  |  |
| Polyglycerin 06 (Comp. Ex. a1) |  |  |  |  |  |  |  |  |  |  | 4 |  |  |  |
| Polyglycerin 10 (Comp. Ex. a2) |  |  |  |  |  |  |  |  |  |  |  | 4 |  |  |
| Polyglycerin X (Comp. Ex. a3) |  |  |  |  |  |  |  |  |  |  |  |  | 4 |  |
| Cell Openert-1 | 1 | 1 | 1 | 1 | 1 | 1 | 1 | 1 | 1 | 1 | 1 | 1 | 1 | 1 |
| Crosslinker-1 | 3 | 3 | 3 | 3 | 1.5 | 1.5 | 1.5 | 1.5 | 1.5 | 3 | 3 | 3 | 3 | 1.5 |
| H2O | 4.1 | 4.1 | 4.1 | 4.1 | 4.1 | 4.1 | 4.1 | 4.1 | 4.1 | 4.1 | 4.1 | 4.1 | 4.1 | 4.1 |
| Catalyst-1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Catalyst-2 | 0.4 | 0.4 | 0.4 | 0.4 | 0.4 | 0.4 | 0.4 | 0.4 | 0.4 | 0.4 | 0.4 | 0.4 | 0.4 | 0.4 |
| Surfactant-3 | 0.7 | 0.7 | 0.7 | 0.7 | 0.6 | 0.6 | 0.6 | 0.6 | 0.6 | 0.7 | 1.2 | 1.2 | 1.2 | 0.6 |
| TOTAL | 113.3 | 113.3 | 113.3 | 113.3 | 109.7 | 109.7 | 109.7 | 109.7 | 109.7 | 109.3 | 113.8 | 113.8 | 113.8 | 107.7 |
| Mass % of Polyol a with respect to 100 of Polyol b | 4 | 4 | 4 | 4 | 2 | 2 | 2 | 2 | 2 | 0 | 4 | 4 | 4 | 0 |
| Density: Core (kg/m3) | 39.0 | 38.8 | 38.5 | 38.8 | 36.8 | 38.4 | 38.3 | 38.3 | 38.5 | 38.8 | 38.5 | 38.9 | 38.6 | 37.4 |
| 25% ILD(N/314 cm2) | 248 | 226 | 226 | 229 | 192 | 194 | 181 | 175 | 179 | 206 | 214 | 214 | 218 | 158 |
| Tensile Strength (kPa) | 117 | 135 | 140 | 121 | 159 | 156 | 158 | 146 | 136 | 146 | 122 | 143 | 136 | 162 |
| Elongation (%) | 59 | 73 | 74 | 66 | 109 | 109 | 104 | 103 | 95 | 96 | 67 | 77 | 74 | 119 |
| Tear Strength (N/cm) | 4.3 | 4.5 | 4.6 | 4.8 | 5.1 | 4.7 | 6.0 | 5.5 | 5.3 | 4.5 | 4.0 | 4.5 | 5.3 | 7.2 |
| 50% Wet Set (%) | 18.9 | 18.6 | 18.3 | 18.3 | 16.2 | 15.6 | 15.6 | 13.6 | 13.0 | 16.9 | 22.8 | 20.4 | 20.1 | 20.7 |
| Ball Rebound: Core (%) | 66 | 67 | 66 | 66 | 67 | 68 | 67 | 68 | 68 | 68 | 66 | 67 | 66 | 66 |

The invention claimed is:

1. A polyol (A) with a molecular weight distribution Mw/Mn of 4 or more, obtained by reacting a compound (II) having a hydroxyl group selected from the group consisting of 2-hydroxytetrahydrofuran, 3-hydroxyoxetane, glycidol, 1,2-epoxy-3-butanol, 3-hydroxycyclopentene oxide, 2,3-epoxy-2-methyl-1-propanol, 2,3-epoxybutanol, 3,4-epoxy-3-methyl-2-pentanol, 3,4-epoxy-4-methyl-2-pentanol, 2,3-epoxycyclohexanol, 2,3-epoxy-4-hydroxyhexane, 6-oxabicyclo [3.1.0]hexane-2,4-diol, 6-oxabicyclo [3.1.0]hexane-2,3-diol, 2,3-epoxy-1,4 butanediol, 1,2-epoxy-3-pentanol, and 2,3-epoxy-4-heptanol in a base polyol (I) with a molecular weight Mn of 2000 or more.

2. The polyol (A) according to claim 1, having at least one peak in the molecular weight distribution curve which exists at a higher molecular weight than that of the base polyol (I).

3. The polyol (A) according to claim 2, wherein the at least one peak existing at a higher molecular weight than that of the base polyol (I) is caused by a polyol which is obtained by an addition polymerization of the compound (II) to a hydroxyl group of the base polyol (I).

4. The polyol (A) according to claim 2, wherein S1/S2 is from 99/1 to 20/80, SI is the area under the peak of the base polyol (I) and S2 is the area under the at least one pack existing at a higher molecular weight that the peak of the base polyol (I).

5. The polyol (A) according to claim 1, wherein the compound (II) comprises an epoxide having a hydroxyl group.

6. The polyol (A) according to claim 5, wherein the epoxide having a hydroxyl group is glycidol.

7. The polyol (A) according to claim 1, wherein a basic compound is used as a catalyst when the compound comprising the compound (II) having a hydroxyl group is reacted in the base polyol (I).

8. A polyol composition, comprising 1 to 200 parts by mass of polyol (A) according to claims 1 and 100 parts by mass of a polyol (B) with a hydroxyl value of 10 to 80 mgKOH/g.

9. The polyol composition according to claim 8, wherein the polyol (B) is at least one polyol selected from polyether polyols and polymer dispersed polyols.

10. The polyol composition according to claim 8, comprising 0.5 to 20 mass % of a constitutional unit derived from the compound (II) in 100 mass % the polyol composition.

11. A flexible polyurethane foam, obtained by reacting the polyol composition according to claim 8 and an isocyanate compound.

* * * * *